(12) United States Patent
Foutz et al.

(10) Patent No.: US 9,014,813 B2
(45) Date of Patent: Apr. 21, 2015

(54) APPARATUS FOR ENERGY EFFICIENT STIMULATION

(75) Inventors: Thomas J. Foutz, Shaker Heights, OH (US); D. Michael Ackermann, San Francisco, CA (US); Cameron C. McIntyre, Cleveland, OH (US)

(73) Assignee: Cleveland Clinic Foundation, Cleveland, OH (US)

( * ) Notice: Subject to any disclaimer, the term of this patent is extended or adjusted under 35 U.S.C. 154(b) by 209 days.

(21) Appl. No.: 13/288,673

(22) Filed: Nov. 3, 2011

(65) Prior Publication Data

US 2012/0239108 A1    Sep. 20, 2012

Related U.S. Application Data

(60) Provisional application No. 61/409,701, filed on Nov. 3, 2010, provisional application No. 61/515,066, filed on Aug. 4, 2011.

(51) Int. Cl.
| | |
|---|---|
| *A61N 1/08* | (2006.01) |
| *A61N 1/36* | (2006.01) |
| *A61N 1/378* | (2006.01) |
| *A61N 1/05* | (2006.01) |

(52) U.S. Cl.
CPC ........... *A61N 1/36125* (2013.01); *A61N 1/0534* (2013.01); *A61N 1/36175* (2013.01); *A61N 1/378* (2013.01)

(58) Field of Classification Search
CPC ........... A61N 1/36142; A61N 1/16142; A61N 1/3615; A61N 1/36153; A61N 1/36189; A61N 1/36192; A61N 1/36196; A61N 1/36171; A61N 1/36175; A61N 1/36178
USPC .......................................... 607/12, 34, 62, 63
See application file for complete search history.

(56) References Cited

U.S. PATENT DOCUMENTS

| | | | | |
|---|---|---|---|---|
| 4,340,063 | A * | 7/1982 | Maurer | 607/46 |
| 4,498,478 | A * | 2/1985 | Bourgeois | 607/13 |
| 6,164,284 | A * | 12/2000 | Schulman et al. | 128/899 |
| 6,289,246 | B1 * | 9/2001 | Money | 607/56 |
| 7,444,181 | B2 | 10/2008 | Shi et al. | |
| 7,444,185 | B1 | 10/2008 | Faltys et al. | |
| 7,519,428 | B1 * | 4/2009 | Palmer | 607/57 |
| 8,116,878 | B1 * | 2/2012 | Palmer | 607/72 |
| 8,121,703 | B1 * | 2/2012 | Palmer | 607/74 |
| 2007/0043400 | A1 * | 2/2007 | Donders et al. | 607/45 |
| 2007/0135868 | A1 * | 6/2007 | Shi et al. | 607/62 |
| 2008/0015657 | A1 * | 1/2008 | Haefner | 607/62 |
| 2008/0114231 | A1 * | 5/2008 | Dai et al. | 600/377 |
| 2010/0211132 | A1 | 8/2010 | Nimmagadda et al. | |
| 2011/0160799 | A1 * | 6/2011 | Mishra et al. | 607/57 |

FOREIGN PATENT DOCUMENTS

WO    WO 2008/004204 A1 *    1/2008

OTHER PUBLICATIONS

The International Search Report and Written Opinion, mailing date May 31, 2012, pp. 1-8.

* cited by examiner

*Primary Examiner* — Allen Porter, Jr.
(74) *Attorney, Agent, or Firm* — Tarolli, Sundheim, Covell & Tummino LLP

(57) ABSTRACT

An apparatus is disclosed for providing efficient stimulation. As an example, a variable compliance regulator can be connected to supply a compliance voltage to a power supply rail, which compliance voltage can vary dynamically based on a stimulus waveform. A pulse generator can be configured to provide an output waveform to one or more output based on the stimulus waveform for delivery of electrical therapy.

35 Claims, 8 Drawing Sheets

APPARATUS FOR ENERGY EFFICIENT STIMULATION

CROSS-REFERENCE TO RELATED APPLICATIONS

This application claims the benefit of U.S. provisional patent application No. 61/409,701, filed Nov. 3, 2010, and entitled EVALUATION OF NOVEL STIMULUS WAVEFORMS FOR DEEP BRAIN STIMULATION and U.S. provisional patent application No. 61/515,066, filed Aug. 4, 2011, and entitled APPARATUS AND METHOD FOR ENERGY EFFICIENT STIMULATION, the entire contents of each of the above-identified applications are incorporated herein by reference.

GOVERNMENT FUNDING

This invention was made with government support under Grant No. NIH R01 NS047388. The U.S. government may have certain rights in the invention.

TECHNICAL FIELD

This disclosure relates to an apparatus for energy efficient stimulation.

BACKGROUND

Electrical stimulation achieves neuromodulation by controlling the release of neurotransmitters in specific parts of the nervous system through induction of action potentials. Electrical stimulation involves transduction of electrical current from the device to ionic current in the nervous tissue. Extracellular methods have been developed to pass current into the tissue, affecting the extracellular voltage potential of the neuronal membrane. These methods typically utilize an implanted neurostimulator to deliver the electrical current.

Implanted electrical neurostimulators draw power from a finite energy supply (e.g., a battery), requiring either frequent recharge cycles or surgical replacement upon full discharge. Accordingly, batteries for conventional electrical neurostimulators must be sufficiently large to meet existing power requirements, which typically results in increased volume for implantable systems.

SUMMARY

This disclosure relates to an apparatus for energy efficient stimulation.

In one example, an apparatus can include a variable compliance regulator connected to supply a compliance voltage to a power supply rail. The variable compliance regulator is configured to dynamically vary the compliance voltage based on a stimulus waveform. A pulse generator is configured to provide an output waveform, corresponding to the stimulus waveform, to at least one output for delivery of electrical therapy based on the compliance voltage.

DETAILED DESCRIPTION

This invention relates to an apparatus for energy efficient stimulation. The apparatus can utilize non-rectangular waveforms to further improve efficiency. In one example, a variable compliance regulator can be connected to supply a dynamic compliance voltage to a power supply rail of a stimulator apparatus. The compliance voltage can vary (e.g., continuously) based on a stimulus waveform. By dynamically varying the compliance voltage in this manner, a pulse generator can provide an output waveform to one or more outputs based on the stimulus waveform for energy efficient delivery of electrical therapy. As disclosed herein, additional improvements in energy efficiency can be achieved through optimizations to other stimulation parameters (e.g., waveform shape and/or pulse width) to further increase the efficiency.

Figure 1:
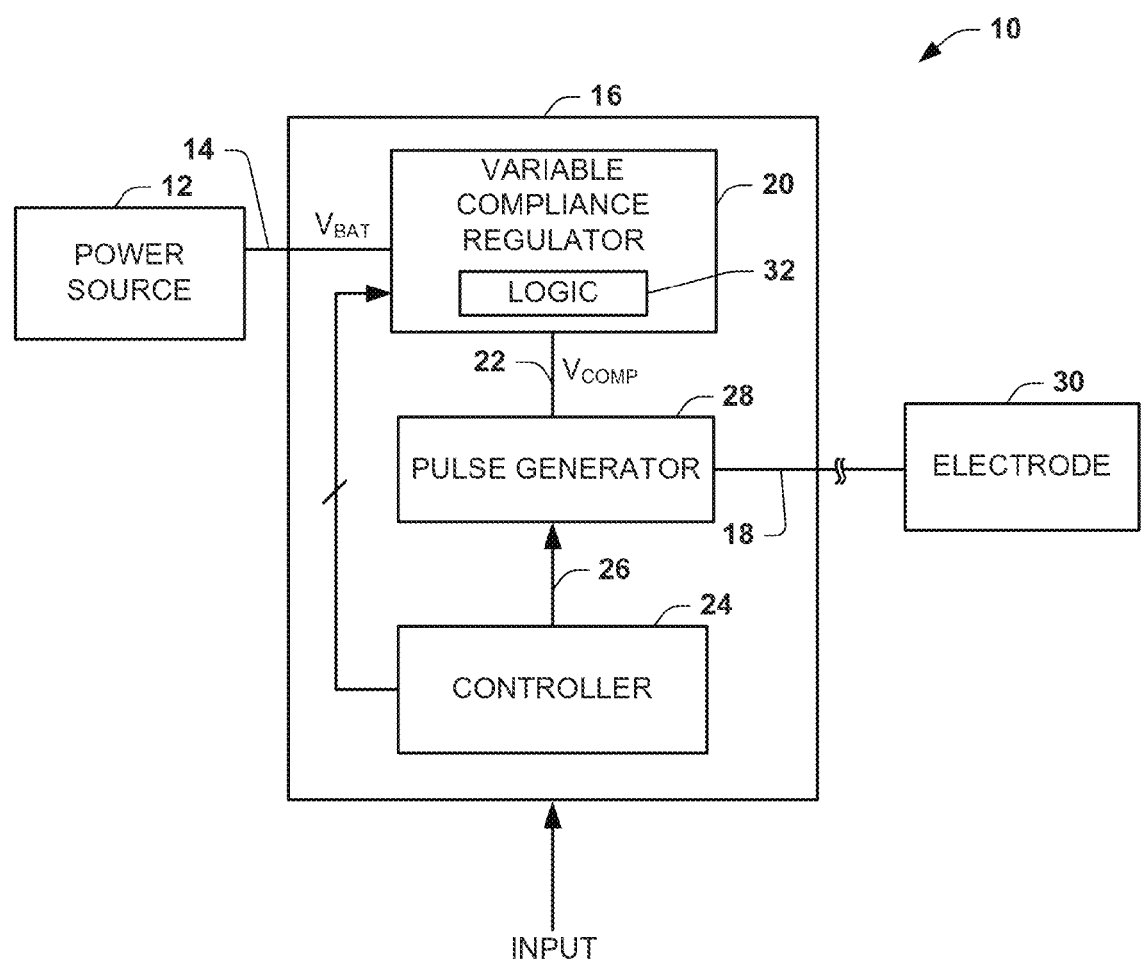
FIG. 1 depicts an example of a block diagram of a stimulation system.

FIG. 1 illustrates an example of a block diagram of a system 10 for providing electrical stimulation. The system 10 includes a power source 12 that supplies power for the system 10. For example, the power source 12 can be a battery that supplies a voltage $V_{BAT}$ to a power input terminal 14 of a stimulation apparatus 16.

The stimulation apparatus 16 is configured to deliver an electrical therapy at one or more outputs 18 thereof. For simplicity of illustration, the example of FIG. 1 includes a single output; although there can be any number of output channels. The system 10, including the power source and the stimulation apparatus 16, can be implemented as an implantable stimulation device in a self-contained housing that is hermetically sealed and capable of percutaneous implantation in a patient (e.g., human or other animal).

The stimulation apparatus 16 can include an arrangement of circuitry that efficiently operates by dynamically managing power consumption during operation. The apparatus 16 includes a variable compliance regulator 20 that is connected to the power input terminal 14. The variable compliance regulator 20 can be implemented as a power converter (e.g., a DC-DC power converter) configured to supply a compliance voltage $V_{COMP}$ to a power supply rail 22. The variable compliance regulator 20 can dynamically vary the compliance voltage $V_{COMP}$ according to an output waveform, as disclosed herein. Pulse generation circuitry 28 can be coupled to the power supply rail 22 to operate based on the compliance voltage $V_{COMP}$. The stimulation apparatus 16 can include one or more other voltage regulators (not shown) that can supply substantially fixed regulated voltage (e.g., a low voltage, such as about 3 V to about 5.5 V) for powering other circuitry in the stimulation apparatus 16.

The apparatus 16 can include a controller 24 configured to control operation of the apparatus. The controller 24 can provides a control signal 26, corresponding to a stimulus waveform, to the pulse generator 28 for controlling the pulse generator to provide an output electrical signal (e.g., a current waveform) at the output 18. As mentioned above, the stimulation apparatus 16 can include one or more outputs 18 corresponding to different output channels that can be controlled independently of each other, such as to provide respective output waveforms to associated electrodes. Each output 18 can be coupled to an electrode 30. Thus, there can be any number of electrodes and each such electrode can be dimensioned and configured according to application requirements. For example, the electrodes can be configured for delivery of electrical therapy to a target site or region in a patient, such as may be in the brain, spinal cord, peripheral nerves, vagus nerve, nerves for controlling bladder function, the heart or the like. In one example, the electrode can be formed of Iridium Oxide or include an Iridium Oxide coating.

The controller 24 can be programmed to define parameters of the stimulus waveform 26 such as based on an input. The input demonstrated in the example of FIG. 1 is intended to represent various types of inputs that stimulation apparatus 16 can receive. For example, the input can be provided from an external device to program the stimulation parameters. The input thus can be provided via a physical connection (e.g., an electrical or optical link) or a wireless connection. Additionally or alternatively, the input can be provided by circuitry (not shown) in the system 10 that provides an indication of one or more sensed parameters (e.g., tissue impedance surrounding the electrode, electrophysiological signals sensed from the patient, feedback, such as voltage or current measurements, from circuitry in the system 10).

For example, the controller can dynamically vary or maintain the output $V_{COMP}$ of the compliance regulator 20 based on feedback measured from other circuit elements in the stimulation path. Such feedback can include voltage or current measurements (e.g. a series component, electrode potential, measured sag in the compliance voltage, potential drop across a current source, e.g., a FET, stimulus current, and the like).

The stimulus waveform parameters for a given output can include amplitude, waveform shape, frequency (e.g., activation time), and pulse width (e.g., duration). Various waveform shapes can be utilized, which can vary depending on capabilities of the system 10 as well as the type and purpose of the electrical therapy being delivered.

Figure 2:
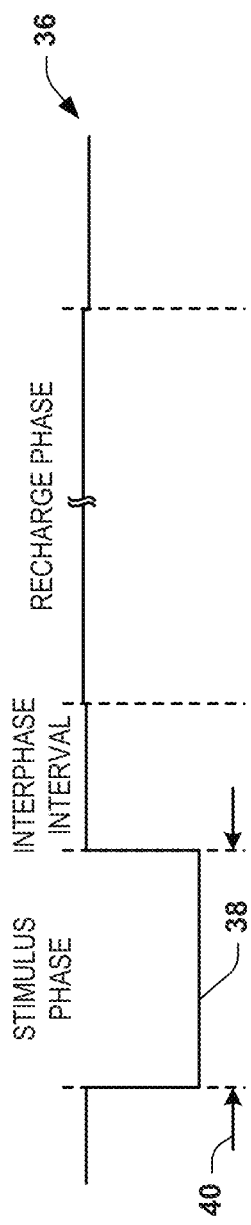
FIG. 2 depicts an example of phases of a stimulation period.

FIG. 2 demonstrates example of a stimulus waveform 36 demonstrating phases of a stimulation period. For example, the stimulation apparatus 16 can use charge-balanced, biphasic, rectangular stimulus waveforms. As shown in the waveform 36, each stimulation period can be composed of three variable phases: a stimulus pulse 38, an interphase interval, and a recharge pulse. The stimulus pulse 38 has an amplitude and pulse width 40, both of which can be programmed according to energy requirements and charge threshold levels, for example. The example of FIG. 2 shows a rectangular pulse; however, it is to be understood that increased energy efficiency according to embodiments disclosed herein, are achieved via non-rectangular waveforms. When considering non-rectangular pulses, the definition of pulse width becomes less clear, and can skew the interpretation of results. For purposes of consistency, the pulse width of each waveform can be represented by the full width at half maximum amplitude (FWHM). As a further example, waveforms can be constructed such that the interphase interval lasts 0.1 ms, followed by a 5.0 ms passive-recharge phase, which coincides with 136 Hz stimulation using modern DBS devices. Other phase timing can also be utilized.

Examples of waveform shapes that can be provided by the controller 24 include rectangular, right triangular, centered triangular, increasing ramp, decreasing ramp, increasing exponential, decreasing exponential, Gaussian, sinusoidal, and trapezoidal to name a few. In response to the stimulus waveforms from the controller 24, corresponding electrical current (or voltage) waveforms can be generated by the pulse generator 28. The waveforms may be analog waveforms or the shapes may be step-wise (e.g., discrete) approximations, which can vary depending on the implementation of the pulse generator 28 and controller 24. Examples of equations that can be used to generate various types of output current waveforms (I) from the pulse generator 28 are provided in the following table, where $\tau_{pw}$ is the desired pulse width, $I_0$ is the amplitude, t is time and a and α are coefficients:

| Waveform Shape | Instantaneous Power |
| --- | --- |
| Rectangular: | $I = I_0$ |
| Sinusoidal: | $I = I_0 \sin(2\pi t/3\tau_{pw})$ |
| Centered triangular: | $I = I_0(1 - abs(t/\tau_{pw} - 1))$ |
| Right triangular: | $I = \dfrac{I_0 t}{2\tau_{pw}}$ |
| Left triangular: | $I = I_0(1 - t/2\tau_{pw})$ |
| Gaussian: | $I = I_0 \dfrac{\exp(at/\tau_{pw} - at^2/\tau_{pw}^2) - 1}{\exp(a/4) - 1}$ |
| Decreasing exponential decrease: | $I = I_0 \dfrac{e^{at/\tau_{pw}} - 1}{e^a - 1}$ |
| Increasing exponential: | $I = I_0 \dfrac{e^{a - at/\tau_{pw}} - 1}{e^a - 1}$ |

Energy and charge requirements can be determined for each waveform and pulse width using a corresponding threshold amplitude. The energy (E) of each cathodic stimulus of the waveform period can be ascertained by integration of the instantaneous power as follows:

$$E = \int_0^{T_c} I^2(t) R \, dt$$

where $T_c$ is the duration of the cathodic phase,
I(t) is the instantaneous current, and
R is the impedance (e.g., assumed constant: about 1 kΩ). As a further example, a passive anodic recharge phase is assumed. Consequently, the foregoing equation presumes to calculate stimulus energy only for the cathodic (stimulus) phase. The charge injected during stimulus can be determined (Q) by integrating the current over the cathodic (e.g., stimulus) phase (Tc):

$$Q = \int_0^{T_c} I(t) \, dt$$

Figure 3:
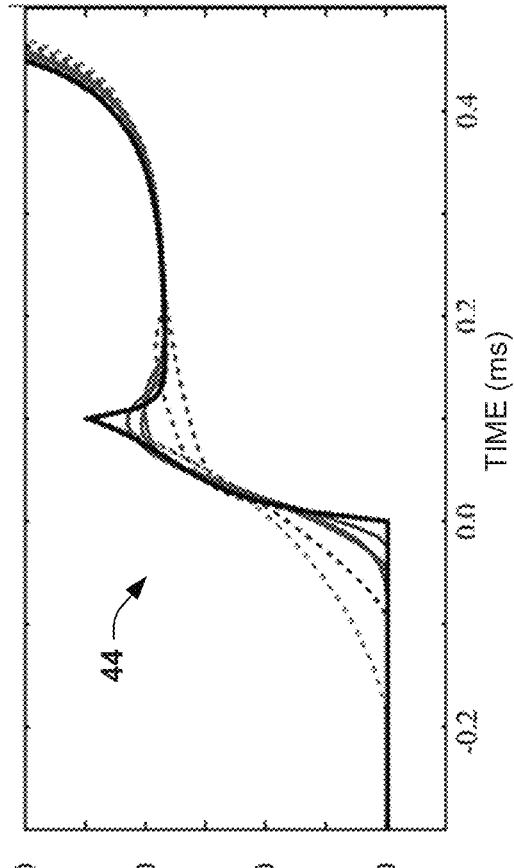
FIG. 3 depicts plots of voltage versus time for different types of waveforms that can be implemented.
Figure 3:
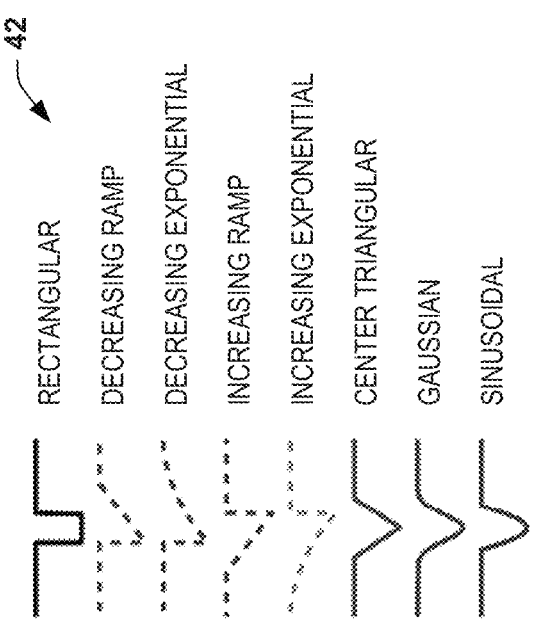

Examples of some stimulus waveforms 42 that can be utilized are shown in FIG. 3. FIG. 3 also illustrates resulting transmembrane voltage responses 44 of axon node to a threshold stimulus using each of the sample stimulus waveforms 42.

As a further example, the input to the controller 24 can set stimulation parameters for a patient. For example, the input can select a type of waveform that is to be applied. The input can also define a pulse width for the stimulus waveform. Alternatively, or additionally, the controller 24 can determine the pulse width based on other information provided via the input. For example, the pulse width can be set as a function of the type of neuron, neuron anatomy (e.g., fiber diameter) and the type of waveform.

Figure 4:
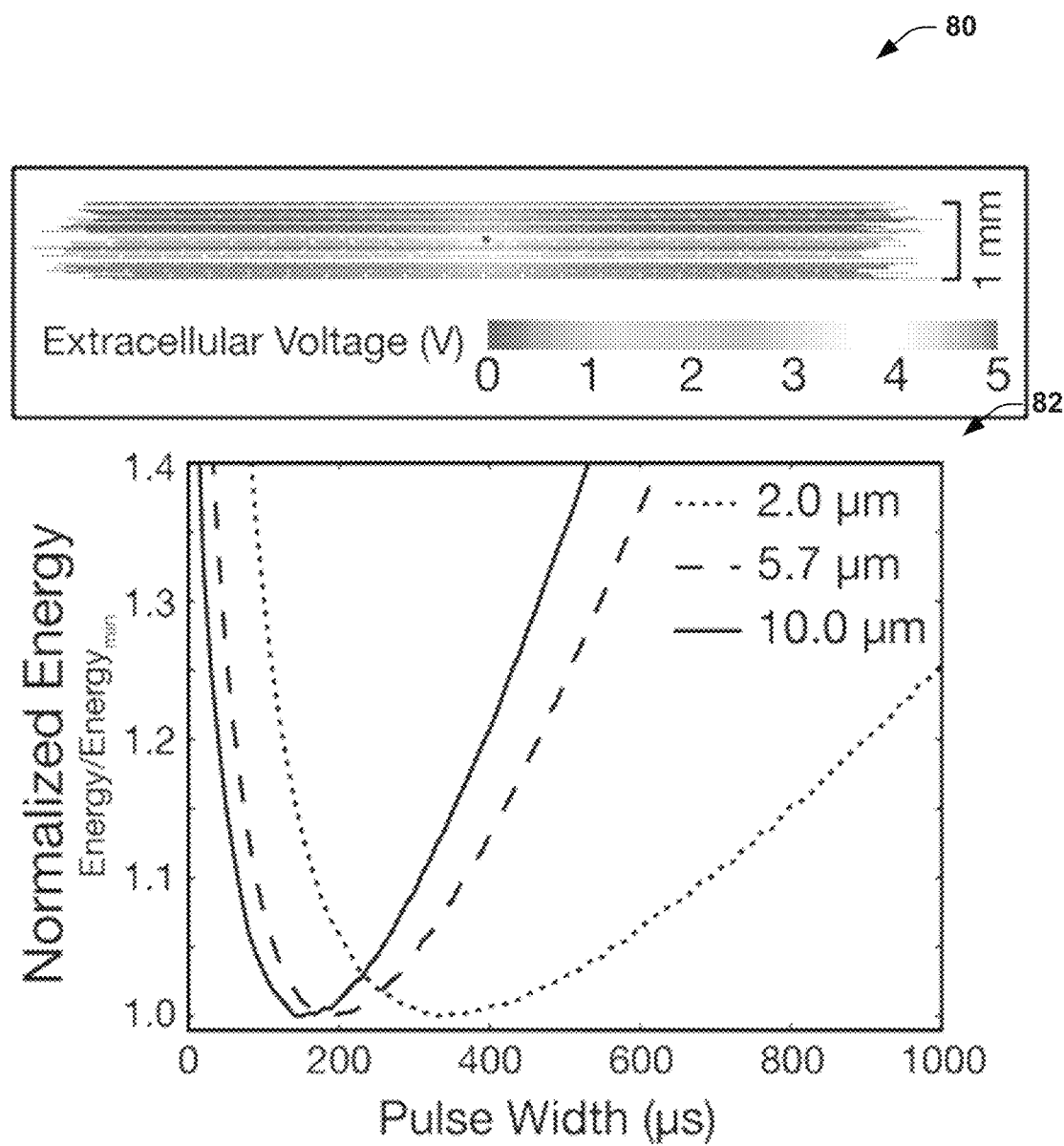
FIG. 4 depicts an example of a graph plotting energy as a function of pulse width for different diameter neurons.

As another example, FIG. 4 depicts an example of a simulated population of fibers, indicated at 80, having varying diameters distributed 1 mm in each direction around a point of origin. The gray-scaling of the fibers represents simulated extracellular voltage in response to apply about 1 mA pulse at a point source located at the origin. Also shown in FIG. 4 is a graph 82 of normalized energy versus pulse width (in μs), which include plots for different diameter fibers. The graph 82 thus demonstrates the dependence of energy on the pulse width for use in stimulating neuron fibers of different diameters. The graph 82 demonstrates the normalized energy as a function of the pulse width for three different size fibers, namely a 2 micron fiber (e.g., stimulated with a pulse width of about 350 μs), a 5.7 micron fiber (e.g., a pulse width about 200 μs) and a 10 micron fiber (e.g., a pulse width of about 170 μs).

As shown in FIG. 4, it can be shown that the pulse widths at which the energy was minimized decreased as the fiber diameter increased. This relationship can be consistent for all fiber diameters (e.g., from about 2 μm to about 16 μm). The mean threshold energy for the most efficient pulse width was 0.21 nJ for large diameter fibers (10.0 μm), exhibited at a pulse width of 180 μs. The largest diameter fibers in this example (16.0 μm) exhibit a nearly identical mean minimum threshold energy (0.18 nJ for 140 μs). The mean minimum energy for small diameter fibers (2.0 μm) may be nearly five times higher (0.98 nJ) for waveforms at a longer pulse width (380 μs). Since peripheral stimulation typically recruits larger diameter neurons, it can be predicted that the energy-optimal rectangular waveforms should have a pulse width in the 100-200 μs range. Alternatively, other types of stimulation (e.g., central stimulation) for smaller diameter fibers may benefit from longer duration pulses, such as having a pulse width in the 300-400 μs range.

As shown in the example of FIG. 4, energy requirements initially dropped as pulse-widths were increased, until they reached a minimum value, at which point they began to increase. This minimum value can be determined for a given application and utilized to program the pulse width of the stimulus waveform. The pulse-width corresponding to this minimum energy threshold varied for each waveform, ranging from about 250 μs (exponentially increasing), to about 500 μs (rectangular).

It has also been determined that an increased pulse width (as compared to a rectangular pulse) can be utilized for non-rectangular pulses. In one example, the centered triangular waveform (e.g., having a larger pulse width of about 500 μs) can minimize energy. Additionally, at short pulse-widths (<200 μs), all non-rectangular waveforms have been determined to be more energy efficient than equal pulse-width rectangular waveforms.

Referring back to FIG. 2, the controller 24 can be programmed to compute the pulse width based on information received via the input or the pulse width can be explicitly defined in the input provided to the controller. The amplitude for the stimulus pulse can also be defined via the input or the controller 24 can be programmed to determine the amplitude depending on the waveform type and pulse width, for example. The set of parameters can thus be optimized for energy efficiency. Thus, the pulse width can be set by the controller 24 to be inversely proportional to a diameter of target neuron fibers to be stimulated. The pulse width can further vary depending on the shape of the waveform that is utilized. In one example, for narrow diameter fibers having a diameter of 6 μm or less (e.g., typically ranging from about 1 μm to about 6 μm for fibers in the central nervous system), the pulse width of a non-rectangular waveform, such as the centered triangular waveform, can be set to greater than or equal to about 200 μs or greater (e.g., ranging from about 200 μs to about 1000 μs). Conversely, for larger diameter fibers having a diameter greater than or equal to about 10 μm (e.g., typically ranging from about 12 μm to about 20 μm), the pulse width of the non-rectangular waveform can be set to less than or equal to 200 μs (e.g., ranging about 50 μs to about 200 μs).

By way of further example, the stimulation parameters can be established in a programming session. For instance, a set of coarse stimulation parameters can be established (e.g., via the input to the controller) initially based on a target volume of activation determined for the patient. The stimulation parameters can then be fine tuned via a calibration process. The calibration process may involve manual, automatic or both manual and automatic calibration methods.

In addition to selecting an energy efficient waveform and stimulation parameters, the programming can also include configuring the variable compliance regulator to operate dynamically. As mentioned above, the variable compliance regulator 20 can dynamically vary the amplitude compliance voltage $V_{COMP}$ commensurate with variations in the amplitude of the stimulus waveform 26 provided by the controller and/or the output waveform provided at 18. For example, the stimulus waveform can be provided to logic (e.g., a FPGA, microcontroller or other circuitry) 32 to generate a control signal to cause the compliance voltage $V_{COMP}$ to follow the shape and amplitude of the stimulus waveform over time.

As an example, if the variable compliance regulator 20 is implemented as DC-DC switched mode (e.g., boost) converter, the stimulus waveform can be combined with a predetermined minimum potential (e.g., via an adder) to provide a combined reference signal. The combined reference signal can be utilized to generate a pulse-width modulated (PWM) signal that controls the output voltage of the converter accordingly. For instance, the PWM signal can be applied to one or more output field effect transistors of the boost converter. The predetermined minimum potential, for example, can correspond to a minimum compliance voltage for other circuitry in the apparatus 16. The minimum compliance voltage can be fixed or it can be variable depending on other operating parameters of the system 10. In this way, the compliance voltage $V_{COMP}$ can continuously vary (e.g., in an analog manner or in discrete steps) during a cathodic portion of the output pulse at 18.

In the foregoing example, it is assumed that the power requirements of the internal circuitry remain substantially constant during delivery of electrical therapy. However, in addition to tracking the shape and amplitude of the stimulus waveform, the variable compliance regulator 20 can optimize the compliance voltage to dynamically vary according to power consumption of other circuitry in the system 10, such as by adjusting the minimum potential based on one or more operating parameters of the system 10. Thus, the variable compliance regulator 20 can vary the compliance voltage dynamically based on a combination of operating parameters, including the waveform shape/amplitude as well as energy requirements of internal circuitry of the apparatus 16 that cooperate to generate the electrical therapy and control other functionality of the system 10. The power utilization of such circuitry further can vary depending on parameters of the electrical therapy being delivered such as pulse width and frequency.

Additionally, the compliance voltage $V_{COMP}$ can be fixed or variable during the anodic phase of the output waveform. During the anodic phase or in between pulses the variable compliance regulator 20 can also substantially optimize the compliance voltage $V_{COMP}$ to accommodate the power consumption of the internal circuitry that is driven by the rail 22. As described above, this can be implemented by dynamically varying the gate signals used to gate output one or more output transistors according to energy requirements of circuitry during the anodic phase.

The controller 24 can also control operation of the variable compliance regulator 20 such as between dynamic, adjustable and fixed modes. The controller 24 can select the mode based on one or more detected operating conditions and provide one or more control signals to the variable compliance regulator 20 for setting the mode of voltage regulation. In the dynamic mode, the variable compliance regulator 20 dynamically varies the compliance voltage based on the stimulus waveform shape. The variable compliance regulator 20 can further dynamically and/or other variable power consumption requirements, as disclosed herein.

In the adjustable mode, the variable compliance regulator 20 can change the compliance voltage between discrete levels (e.g., a higher voltage during the pulse and a lower voltage between pulses) but the compliance voltage is not continuously varied as in the dynamic operating mode. In the fixed mode, the regulator maintains the compliance voltage at a predetermined fixed level.

As another example, the controller 24 can compare the peak stimulation amplitude for a selected stimulus waveform. If the peak stimulation amplitude requires a compliance voltage that is less than the battery voltage $V_{BAT}$, the controller 24 can operate the variable compliance regulator 20 in the fixed mode. If the controller 24 determines that peak stimulation amplitude exceeds the battery voltage $V_{BAT}$ but by an amount that is less than a predetermined threshold voltage, the controller can operate the variable compliance regulator 20 in the adjustable mode. The predetermined threshold voltage can be programmed to correspond to the expected additional energy consumption that results from implementing the dynamic mode relative to the energy consumption in the adjustable mode (e.g., $V_{THRESHOLD} \sim ENERGY_{DYNAMIC} - ENERGY_{ADJUSTABLE}$). Thus, the adjustable mode can be utilized in situations when the additional increase in energy consumption for implementing the dynamic mode over the adjustable mode would not result in an increase in energy efficiency.

Figure 5:
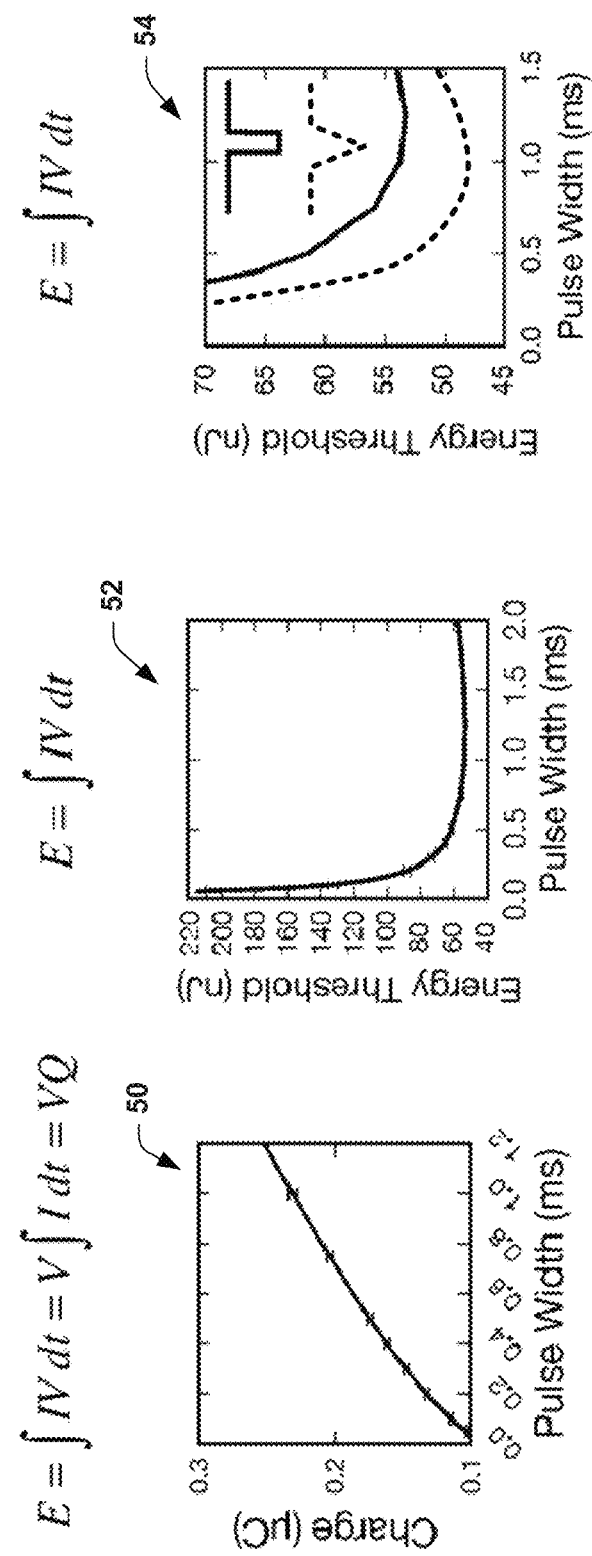
FIG. 5 depicts examples of plots demonstrating a comparison for different energy utilization strategies.

FIG. 5 depicts graphs demonstrating examples of different energy optimization strategies that can be implemented in an implantable pulse generator (IPG) based on the teachings hereon. In the example of FIG. 5, a graph 50 plots charge (in μC) versus pulse width, for a stimulation apparatus implementing a fixed compliance voltage. As shown, since energy is equal to voltage times charge, this results in generally monotonically increasing charge requirements with longer pulse widths. This remains true with different waveform types although the energy requirements differ.

Other graphs 52 and 54 in FIG. 5 plot an energy threshold (in nJ) versus pulse width (in ms) for both an stimulation apparatus (e.g., apparatus 16 of FIG. 1) implementing an adjustable compliance voltage (e.g., an adjustable mode) and dynamic compliance voltage (e.g., a dynamic mode), respectively. The energy threshold corresponds to an amount of energy required to achieve a percentage of activation. A comparison between the plot 52 for the adjustable compliance voltage and the plot 54 for the dynamic compliance voltage demonstrates a significance decrease in energy as a function of pulse width with the dynamic compliance voltage.

Additionally, the graph 54 for the dynamic compliance voltage example demonstrates how different pulse shapes results in different energy thresholds over a range of pulse widths. For example, the graph 54 includes plots for two example stimulus waveform shapes, namely, a rectangular stimulus waveform and a centered triangular waveform. From the plots in the graph 54, it is demonstrated that a centered triangular waveform results in a decreased energy threshold for a given pulse width as compared to a conventional rectangular waveform.

Figure 6:
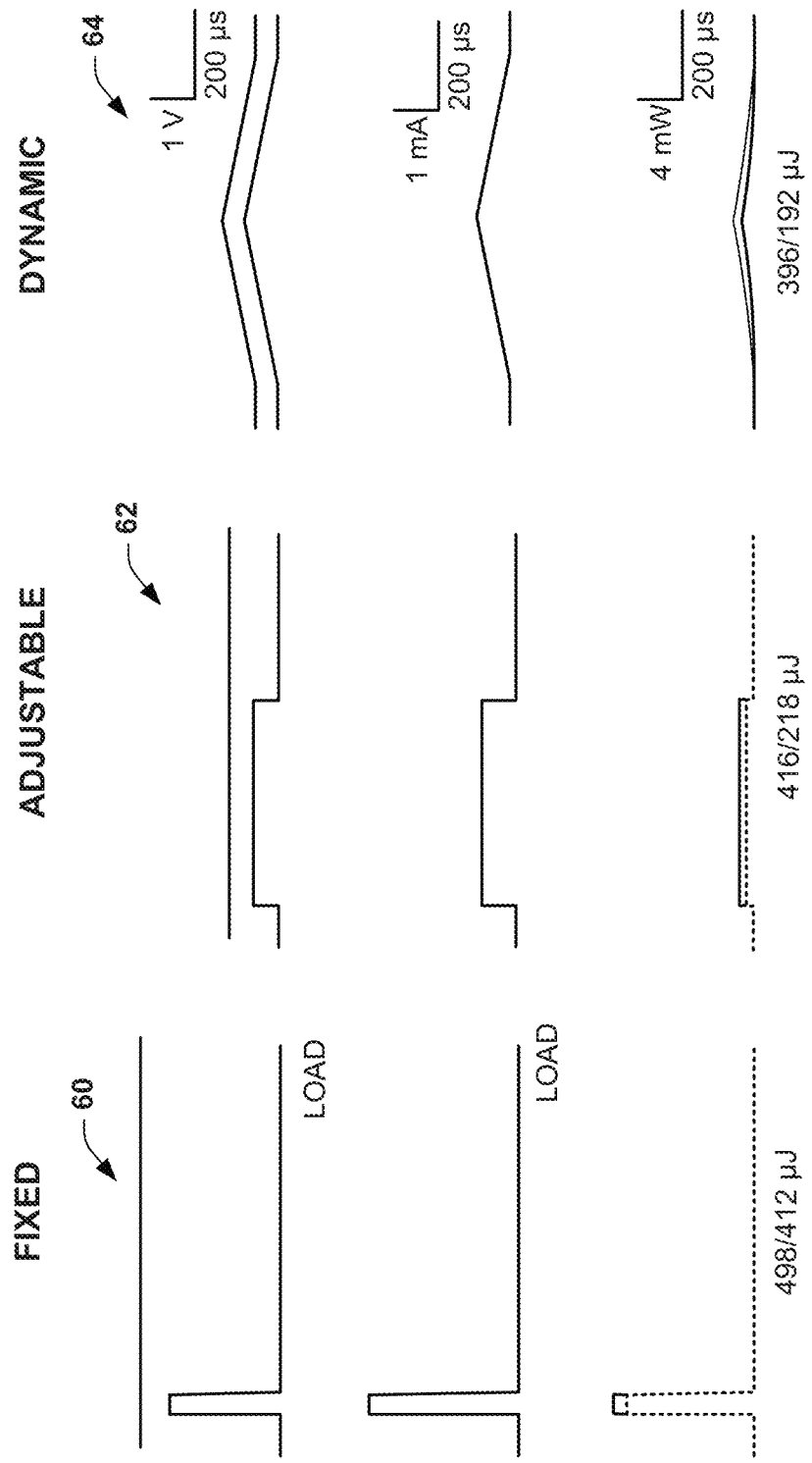
FIG. 6 depicts an example of graphs of power, current and voltage demonstrating a comparison between fixed, adjustable and dynamic compliance voltages.

FIG. 6 demonstrates additional examples of graphs power, current and voltage for each of a fixed compliance voltage, adjustable compliance voltage and dynamic compliance voltage, indicated at 60, 62 and 64, respectively. Each of the example graphs 60, 62 and 64 further demonstrates differences between the load power and voltage and the compliance power and voltage, respectively. For example, in the adjustable compliance voltage scenario 62 the power for the compliance voltage is about 416 μJ, whereas the load power was about 218 μJ. In contrast, for the centered triangular waveform employed in the dynamic compliance voltage example 64, the power due to the dynamic compliance is about 396 μJ and the power due to the load is about 192 μJ. Thus, the example of FIG. 6 demonstrates the power savings associated with a dynamic compliance voltage verses each of a fixed and adjustable compliance voltage. Additionally, a larger pulse width can be utilized for the dynamic compliance voltage than in cases where either a fixed or adjustable compliance voltage is used. Thus, as a result of the dynamic compliance voltage, a user can selectively determine a desired width for target tissue to be stimulated, which is in contrast to systems utilizing a fixed compliance voltage.

Figure 7A:
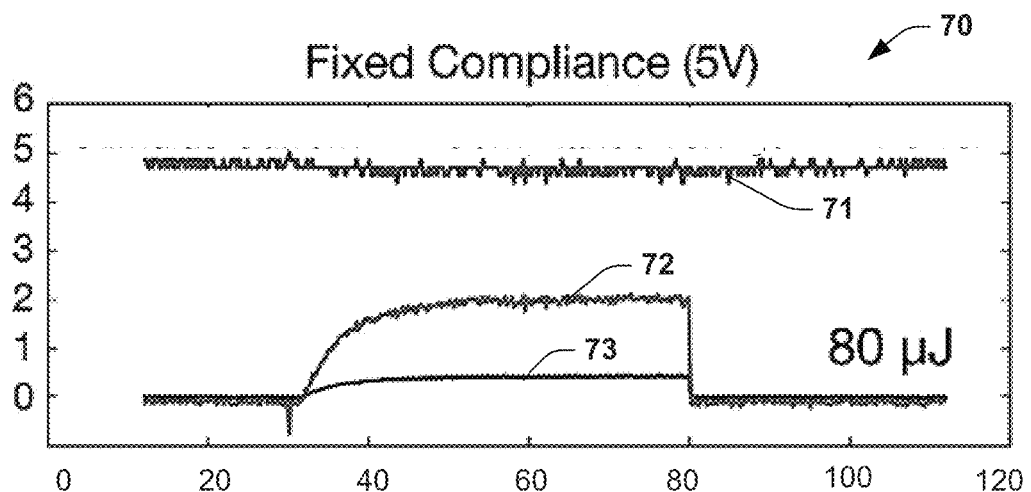
FIGS. 7A and 7B depict an example of output waveforms for a stimulator demonstrating a comparison between operating with a fixed compliance voltage and a variable compliance voltage.
Figure 7B:
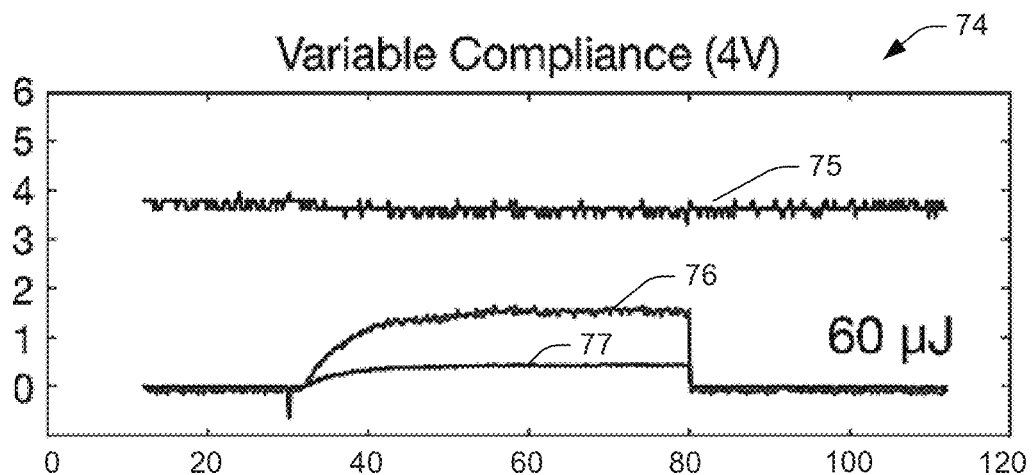

FIGS. 7A and 7B demonstrate examples of graphs 70 and 74 for output waveforms for fixed and variable compliance voltages. In FIG. 7A, the graph 70 includes plots of a fixed compliance voltage 71 (e.g., 5 V) and resulting power 72 and stimulus current 73. In FIG. 7B, the graph 74 includes plots of the compliance voltage 75 (e.g., about 4 V) and resulting power 76 and stimulus current 77. In each of these example graphs 70 and 74, the same type of stimulus waveforms and pulse width were used, but due to the reduced compliance voltage it is shown that a power savings of about 20 μJ can be achieved using the variable compliance voltage given the same output waveforms. Further power savings can be achieved by employing a dynamically varying compliance voltage and/or employing a non-rectangular waveform (e.g., centered-triangular waveform) as disclosed herein.

Figure 8:
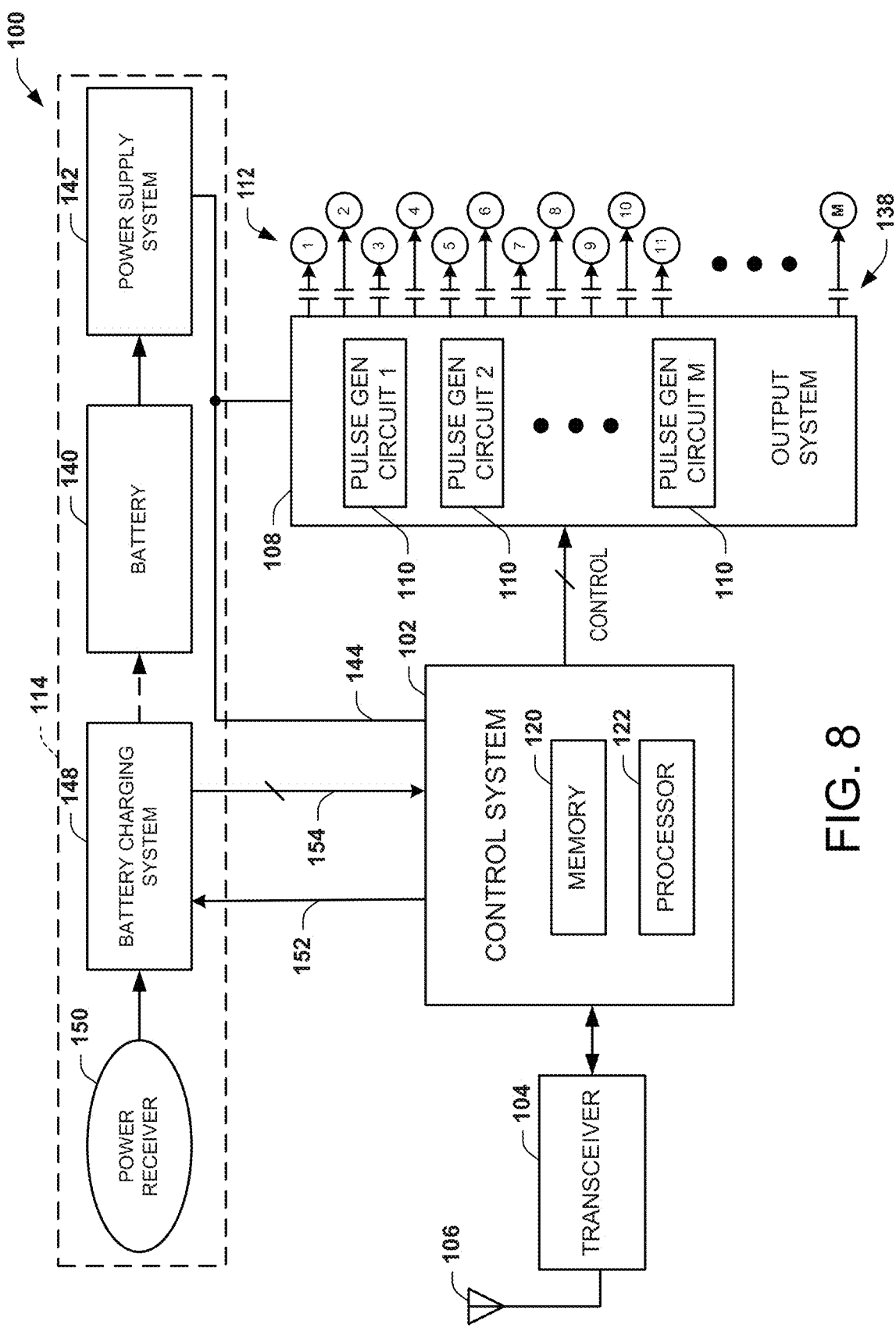
FIG. 8 depicts an example of another stimulation system that can be implemented.

FIG. 8 depicts an example of an implantable pulse generator (IPG) system 100 that can be implemented. The IPG system 100 is configured to deliver electrical stimulation to target tissue via one or more output channels 112. In the example of FIG. 3, IPG the system 100 includes a control system 102 that is operative to control application of stimulus pulses. The control system 102 can also control a compliance voltage, such as disclosed herein. The control system 102 can be implemented as a microcontroller unit (e.g., an integrated circuit) or as a combination of one or more integrated circuits (e.g., analog and digital circuitry) that can be programmed and/or configured to implement the functions described herein.

The control system 102 can be coupled to a transceiver 104. The transceiver 104 can be coupled to an antenna 106 for implementing wireless communications to and from the IPG system 100. As used herein, the term "wireless" refers to communication of information without a physical connection for the communication medium (the physical connection usually being electrically conductive or optical fiber). As described herein, the transceiver 104 alternatively could be implemented as a hard wired connection (e.g., including electrically conductive and/or optical links). Those skilled in the art will understand and appreciate various types of wireless communication modes that can be implemented by the transceiver 104, such as described herein. As an example, the transceiver 104 can be programmed and/or configured to implement a short range bi-directional wireless communication technology, such as Bluetooth or one of the 802.11x protocols.

The control system 102 is connected to provide one or more stimulus waveforms to an output system 108. The output system 108 is connected to receive the stimulus waveforms from the control system 102 and provide corresponding output electrical waveforms, such as in the form of pulses to associated loads. The output system 108 can include one or more pulse generator circuits 110, demonstrated as including M circuits, where M is a positive integer. Each of the pulse generator circuits 110 can provide the output electrical signals (e.g., current pulses) to a set of one or more corresponding output channels 112 according to the stimulus waveform provided by the control system 102. The output channels 112 may include output ports electrically coupled directly with respective electrodes or other peripheral devices coupled to receive the output waveforms from the IPG system 100. For example, the output stages corresponding to the pulse generation circuits 110 can be configured to deliver electrical current over a range from 1 µA to 20 mA.

The IPG system 100 can also include a power system 114 that is operative to supply a compliance voltage to a power rail for operation of the various circuitry in the IPG. Each of the pulse generator circuits 110 as well as other circuitry in the IPG 100 can be coupled to the power supply rail 144 corresponding to the compliance voltage. As disclosed herein, the compliance voltage can be a dynamic voltage. Additionally, the power system 114 can operate in multiple modes, such as including the fixed compliance mode, adjustable compliance mode and dynamic compliance mode disclosed herein. While a single rail is shown, it will be understood that, depending on voltage requirements of the circuitry in the system 100, there can be more than one rail, each of which may be independently controlled to provide a regulated voltage that can be fixed, adjustable and/or may be dynamically varied as disclosed herein.

The control system 102 can include memory 120 and a processor 122. The memory can include data and instructions that are programmed to control operation of the IPG 100, such as may vary according to application design requirements of the IPG. The processor 122 can access the memory and execute the instructions stored therein. Alternatively, the control system 102 can be a hardware design, such as configurable logic (e.g., a field programmable gate array (FPGA) or the like) that can be configured to function as disclosed herein. While the control system 102 is demonstrated as an integrated unit, some of the functionality and related circuitry (e.g., sensors—not shown) that provide inputs to the control system could be implemented as an external components implemented external to an integrated circuit comprising the control system.

The control system 102 can also control operation of the transceiver 104, such as through a corresponding interface. As an example, during a programming mode, the control system 102 can receive and send information via the transceiver 104 for programming stimulation parameters for the IPG 100. Alternatively, some or all of the IPG operating parameters can be pre-programmed. The programmable operating parameters can include, for example, waveform type, amplitude, pulse width, frequency, as well as control the number of pulse trains that are supplied to the output system 108 for delivery of electrical therapy. The control system 102 can modify such operating parameters during operation to provide a modified version of the waveform (e.g., the modifications being based on feedback to provide for closed loop operation or based on external user input via the transceiver).

The control system 102 can also control which of the plurality of output channels 112 are provided with corresponding output stimulus waveforms. For example, the output system 108 thus can selectively distribute output waveforms to one or more of the output channels 112 based upon the control instructions that define how such distribution is to occur.

As described herein, one or more electrodes can be coupled to each of the corresponding output channels 112 for delivering corresponding electrical therapy based on the waveforms provided to the corresponding outputs by the respective pulse generator circuits 110. The size and the configuration of the output system 108 can vary according to the number of output channels. In this example, the energy available to the electrical components varies according to the compliance voltage that can be dynamically varied by the power system 114.

As a further example, the pulse generator circuits 110 can be implemented as current pulse generators configured to provide electrical current to each output channel to which one or more electrodes can be connected. To mitigate interference between the respective output channels 112, DC blocking capacitors 138 can be connected between the output system 108 and the corresponding ports of the output channels 112. The DC blocking capacitors can also mitigate sustained delivery of DC current. The DC blocking capacitors 138 can be selected to have a corresponding capacitance based upon the desired frequency range at which the output signals are to be supplied to the corresponding output channels 112.

The power system 114 includes a battery 140 that stores a charge for providing corresponding DC voltage to the IPG system 100. For example, the battery 140 supplies the DC output voltage to the power supply system 142, which provide a compliance voltage to power rail 144. The amount of voltage provided the battery 140 can vary according to the power requirements of the IPG system 100. The battery can be rechargeable.

The power supply system 142 can also include load tracking and switch mode power supplies for providing appropriate power to the various parts of the IPG system. As disclosed herein, the power supply system 142 can be a DC-DC boost converter that dynamically varies the voltage rail 144 available to the output system 110 and other circuitry as a function of the particular stimulus waveform(s) being provided by the control system 102 to the output system 108. For example, the control system can provide a control signal based on one or more of the stimulus waveform and other operating parameters in response to which the power supply system 142 dynamically varies the compliance voltage at the rail 144.

The output system 108 can also provide feedback to the control system 102. As one example, the feedback can provide an indication of the output impedance for the respective output channels (e.g., including the impedance of the electrodes connected at the respective output channels and/or the impedance at the tissue/electrode interface). The control system 102 or other circuitry can determine the impedance, for example, as a function of a voltage or current signal corresponding to the feedback. For example, the feedback can be utilized to fine tune the compliance voltage to increase the energy efficiency of the IPG 100.

The control system 102 can also employ the transceiver 104 for transmitting appropriate information when the feedback indicates these and other sensed conditions may reside outside of expected operating parameters. The control system 102 can initiate transmission of the information automatically in response to detecting operation outside of expected operating parameters. Alternatively, the control system 102 can store such information (e.g., in the memory) and transmit in response to being interrogated by a corresponding external transmitter or external transceiver.

The power system 114 can also include a battery charging system 148 and a power receiver 150. The battery charging system 148, for example, may include charging control circuitry for the battery 140 as well as a power converter (e.g., including a rectifier) that is operative to convert the power received by the power receiver 150 to an appropriate form and level to facilitate charging the battery 140. In this regard, the battery 140 can be a rechargeable type, such as a lithium battery, or nickel cadmium battery capable of extended use between charges. Alternatively, the battery 140 may be replaceable (e.g., surgically or otherwise).

The power receiver 150, for example, can be implemented as a inductive power pick-up such as including an inductive coil and other appropriate circuitry that can receive, filter and couple power (e.g., via mutual inductance) from a corresponding power transmitter that may be placed adjacent or in contact with the power receiver. The power receiver 150 and the battery charging system 148 can be implemented as an integrated system to facilitate charging the battery 140. Additionally, the control system 102 can control the battery charging system 148 in response to the feedback. For example, the control system 102 can provide corresponding control signals 152 to the battery charging system 148 through a corresponding interface. Additionally, the current and/or voltage associated with the charging of the battery (or other parameters associated with operation of the charging system) can be monitored by the control system 102 via one or more corresponding analog inputs 154. The control system 102 can control the battery charging process in response to the voltage and/or current characteristics associated with the charging process, as detected via the input 154.

Figure 9:
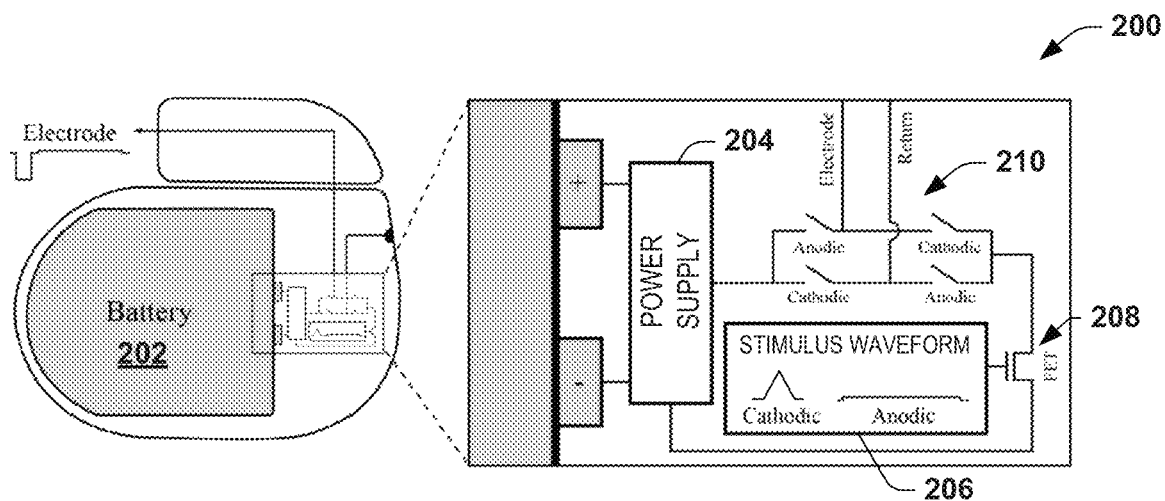
FIG. 9 depicts an example of an implantable pulse generator device.

FIG. 9 depicts an example of an IPG device 200 as a self-contained unit (e.g., corresponding to the system 10 of FIG. 1 or system 100 of FIG. 8). The IPG device 200 contains many components, including a battery 202, a power supply 204, a stimulus waveform generator (e.g., a controller) 206, an output transistor 208 for generating current and output switches 210, as schematically demonstrated in FIG. 7 and otherwise disclosed herein. For example, the cathodic and anodic waveform from waveform generator 206 can drive the transistor 208 to supply a corresponding output current waveform, as disclosed herein, and transistor switches 210 can be used to set the polarity of the output waveform in response to switching control signals.

Stimulator designs can vary depending on the device objectives, such as size, battery life, and application. In the case of DBS, the IPG can be implanted subcutaneously below the clavicle. The IPG 200 is hermetically sealed, and is powered by a medical grade energy cell (battery). The IPG 200 may have a rechargeable battery, which typically requires recharging daily or weekly. In other embodiments, an IPG may have a non-rechargeable battery, requiring surgical replacement every 3-6 years. The battery lifetime (or recharge interval) is dependent on the rate at which energy is consumed by each of the IPG circuit elements. Of all the neural stimulator's functions, stimulation is the largest energy consumer, and is therefore a primary target for increasing energy efficiency. Thus the approach disclosed herein for dynamically varying the compliance voltage for the IPG 100 can significantly increase energy efficiency.

Figure 10:
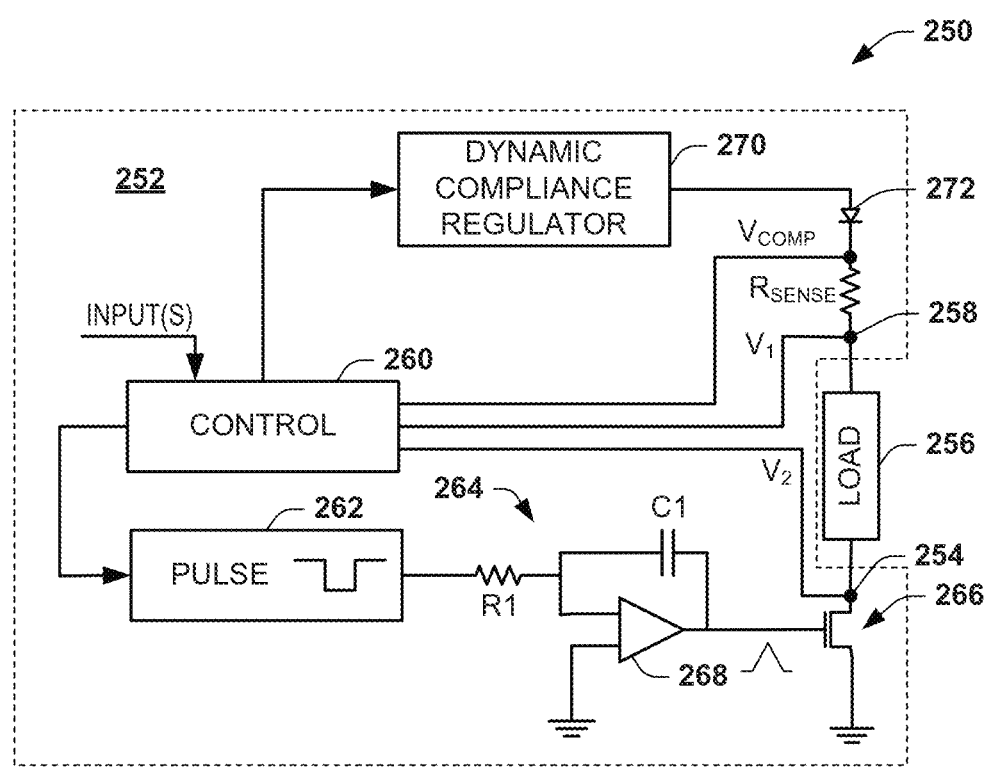
FIG. 10 depicts an example of a pulse generation circuit that can be utilized to generate a centered triangular waveform.

FIG. 10 depicts an example of a stimulation system 250 that can be implemented. The system 250 includes a stimulation apparatus 252 configured to provide an electrical stimulation waveform to an output 254 coupled to a load 256. In this example, the load 256 can include one or more electrodes as well as tissue in which the electrode can be positioned. The load is depicted as being coupled between output nodes 254 and 258. The stimulation apparatus 252 can correspond to the stimulation apparatus 16 of FIG. 1 or the control system 102 of FIG. 8. In the example of FIG. 10, the stimulation apparatus 252 is configured to provide a non-rectangular (e.g., centered triangular) waveform and to do so based on a dynamically varying compliance voltage.

By way of example, the stimulation apparatus 252 includes a controller 260. The controller 260 can provide a control pulse 262 or control associated circuitry (e.g., pulse generator or latch circuit) to provide such pulse. The control pulse 262 can be supplied to stimulus pulse generating circuitry 264 for providing the stimulus waveform to drive a current generator 266, depicted in FIG. 10 as a field effect transistor. The current generator 266 thus provides an output electrical signal (e.g., a current waveform) at the output 254 for providing corresponding current waveform to the load 256. The load 256 can represent one or more electrodes, surrounding tissue that affects the output signal provided at 254 or other influences on the electrical path between outputs 254 and 258. The output waveform thus can further vary based on the electrical characteristics (e.g., impedance) of the load. As mentioned above, the stimulation apparatus 252 can include any number of one or more outputs 254 and 258, each corresponding to different output channels. Each channel can be controlled independently of each other, such as to provide respective output waveforms to associated electrodes.

In the example of FIG. 10, the circuitry 264 is configured to generate a centered-triangular waveform. However, the circuitry 264 could be configured (or be programmable) to provide other shapes of waveforms disclosed herein. The circuitry 264 includes an input resistor R1 coupled to an input of an operation amplifier 268. A capacitor C1 is coupled between the input and output of the op-amp 268 and the other op-amp input is coupled to ground to provide an integrator. Thus, the circuitry 264 provides a centered triangular waveform to the current generator 266 in response a rectangular signal at its input. The parameters of the rectangular signal can be controlled by the controller 260 to set corresponding parameters in the stimulus waveform.

The controller 260 can also monitor voltages V1 and V2 at outputs coupled to the load 256 as well as a compliance voltage $V_{COMP}$ provided by a dynamic compliance generator 270 through a diode 272. A current sense resistor $R_{SENSE}$ can be coupled between the outputs 254 and 258, such that the controller can monitor current delivered to the load based on the potential across the resistor $R_{SENSE}$ (e.g., $V_{COMP}$–V1). The controller 260 can also receive other inputs based on which it can control operation of the system 250, as disclosed herein (see, e.g., description of FIG. 1). The inputs can include feedback of sensed operating parameters and the like. The controller 260 thus can control the dynamic compliance regulator 270 as well as control of the pulse 262 based on the inputs or other measured signals. In another example, the circuitry 264 may include a variable resistance and/or variable capacitance, such that the controller 260 can vary such components to implement further control of the stimulus waveform shape.

In view of the foregoing structural and functional description, those skilled in the art will appreciate that portions of the invention (e.g., control functionality) may be embodied as a method, data processing system, or computer program product. Accordingly, these portions of the present invention may take the form of an entirely hardware embodiment, an entirely software embodiment, or an embodiment combining software and hardware. Furthermore, portions of the invention may be a computer program product on a computer-usable storage medium having computer readable program code on the medium. Any suitable computer-readable medium may be utilized including, but not limited to, static and dynamic storage devices, semiconductor storage devices, hard disks, optical storage devices, and magnetic storage devices.

While the foregoing examples disclose dynamically varying the compliance voltage, corresponding to a voltage rail, which is used to supply an output waveform, similar effects can be achieved in a system that does not employ a compliance voltage per se. For example, a corresponding voltage rail can itself operate as the current driver for delivery of the output waveform to the load. In this implementation, the controller (e.g., the controller 24 of FIG. 1 or control system 102 of FIG. 2) can adjust a corresponding voltage driver, which is coupled to provide an output voltage to the rail, based on the stimulus waveform. For instance, the controller can dynamically vary the voltage rail (via its control of the voltage driver) as to maintain the current through the load based on a sensed parameter (e.g., a feedback measurement from the load). This could be implemented in the context of FIG. 10 by replacing the regulator 270 with a dynamic voltage driver, removing the current generator 266 and configuring the controller with the functionality as just described. In this way, a dynamic voltage pulse generator can be configured to provide a voltage output waveform, corresponding to a current stimulus waveform, where the voltage delivered by the stimulator is adjusted to maintain a constant load current, and the pulse generator voltage is adjusted dynamically (e.g., continuously in real time) in response to a current feedback measurement. The current feedback can be from the load itself or another element (e.g., a current sense resistor) in series with the load.

What have been described above are examples. It is, of course, not possible to describe every conceivable combination of components or methodologies, but one of ordinary skill in the art will recognize that many further combinations and permutations are possible. Accordingly, the invention is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. An apparatus, comprising:
    a variable compliance regulator connected to supply a compliance voltage to a power supply rail, the variable compliance regulator being configured to dynamically vary the compliance voltage over time to track a waveform shape and amplitude of a time-varying stimulus waveform; and
    a pulse generator coupled to receive power from the power supply rail and configured to provide an output waveform to at least one output port in response to the stimulus waveform provided to a control input thereof, the output waveform having a waveform shape and amplitude corresponding to the waveform shape and the amplitude of the time-varying stimulus waveform and having energy that varies as a function of the compliance voltage.

2. The apparatus of claim 1, wherein the waveform shape of the time-varying stimulus waveform comprises a pulse shape, the variable compliance regulator varies the compliance voltage dynamically to follow the pulse shape of the time-varying stimulus waveform for at least a cathodic portion of the stimulus waveform.

3. The apparatus of claim 2, wherein the compliance voltage dynamically varies continuously as a function of the pulse shape of the time-varying stimulus waveform.

4. The apparatus of claim 2, wherein the compliance voltage dynamically varies in discrete steps as a function of the pulse shape of the time-varying stimulus waveform.

5. The apparatus of claim 1, further comprising a controller configured to provide the time-varying stimulus waveform to the pulse generator to control the output waveform.

6. The apparatus of claim 5, wherein the controller is programmed to supply the time-varying stimulus waveform with a pulse width according to at least one of a location of an electrode relative to a target, neuron type to be stimulated or waveform characteristics.

7. The apparatus of claim 6, wherein the waveform characteristics correspond to a type of cathodic stimulus waveform.

8. The apparatus of claim 7, wherein the type of cathodic stimulus waveform comprises at least one of a Gaussian waveform, right triangular waveform, centered triangular waveform, a rectangular waveform, a sinusoidal waveform, an increasing ramp waveform, a decreasing ramp waveform, an increasing exponential waveform and a decreasing exponential waveform.

9. The apparatus of claim 5, wherein the controller is further configured to control operation of the variable compliance regulator to enable the compliance voltage to continuously vary the output waveform.

10. The apparatus of claim 9, wherein, if a peak current delivery of the electrical therapy involves less voltage than available from a power supply, the variable compliance regulator is configured to provide a substantially fixed compliance voltage to the supply rail.

11. The apparatus of claim 5, wherein the controller dynamically controls the output of the compliance regulator based on a sensed parameter.

12. The apparatus of claim 11, wherein the sensed parameter corresponds to a sensed signal from circuitry in a stimulation path of the apparatus.

13. The apparatus of claim 11, wherein the sensed parameter corresponds to a characteristic of biological tissue at a target site.

14. The apparatus of claim 1, further comprising a power source coupled to provide a battery voltage to the variable compliance regulator.

15. The apparatus of claim 1, further comprising an output stage configured to provide an output current to the at least one output port in response to the output waveform and based on the compliance voltage.

16. The apparatus of claim 15, wherein the output stage is configured to deliver electrical current over a range from 1 μA to 20 mA.

17. The apparatus of claim 15, further comprising at least one electrode coupled to the at least one output port, the pulse generator being configured to deliver the electrical therapy via the at least one electrode and with a pulse width that depends on an area of the at least one electrode.

18. The apparatus of claim 1, wherein the variable compliance regulator is configured to operate in a mode selected from one of a dynamic operating mode, an adjustable operating mode and a fixed operating mode, the mode being selected based on a detected operating parameter.

19. The apparatus of claim 1, further comprising a controller configured to provide the stimulus waveform and thereby control the output waveform as a centered triangular waveform having a pulse width that is set according to a diameter target neuron fibers to be stimulated, the controller being configured to control at least one waveform parameter of the stimulus waveform based on at least one sensed parameter.

20. An implantable pulse generation system comprising the apparatus of claim 1, the system comprising an output system where the pulse generator comprises a plurality of pulse generator circuits coupled to the power supply rail, wherein each pulse generator circuit provides a corresponding output waveform to an associated output channel for delivering the electrical therapy.

21. The apparatus of claim 1, further comprising a controller configured to further control each of the time-varying stimulus waveform and the variable compliance regulator based on feedback indicative of one or more sensed parameters.

22. An implantable pulse generation system, comprising:
a variable compliance regulator connected to supply a compliance voltage to a power supply rail, the variable compliance regulator being configured to dynamically vary the compliance voltage over time to follow a waveform shape and amplitude of a stimulus waveform; and
a stimulation apparatus coupled to the power supply rail, comprising:
a controller configured to generate the stimulus waveform comprising a non-rectangular pulse shape;
a pulse generator coupled to the power supply rail and configured to provide an output waveform to at least one output port in response to the stimulus waveform, the output waveform having a waveform shape and amplitude corresponding to the waveform shape and the amplitude of the stimulus waveform and having energy that varies as a function of the compliance voltage.

23. The system of claim 22, wherein the compliance voltage dynamically varies continuously as a function of the waveform shape and the amplitude of the stimulus waveform.

24. The system of claim 22, wherein the compliance voltage dynamically varies in discrete steps as a function of the waveform shape and the amplitude of the stimulus waveform.

25. The system of claim 22, wherein the variable compliance regulator is configured to operate in a selected one of a dynamic operating mode, an adjustable operating mode and a fixed operating mode, the mode being selected based on a detected operating condition.

26. The system of claim 22, wherein the non-rectangular pulse shape comprises at least one of a Gaussian waveform, right triangular waveform, centered triangular waveform, a sinusoidal waveform, an increasing ramp waveform, a decreasing ramp waveform, an increasing exponential waveform and a decreasing exponential waveform.

27. The system of claim 22, wherein the controller is configured to dynamically control the variable compliance regulator based on a sensed parameter.

28. The system of claim 27, wherein the sensed parameter corresponds to at least one of a sensed signal from circuitry in a stimulation path of the system and a characteristic of biological tissue at a target site.

29. The system of claim 28, wherein the non-rectangular pulse shape comprises a centered triangular waveform, the controller controlling parameters of the stimulus waveform based on at least one sensed parameter to mitigate power consumption.

30. The system of claim 29, wherein the centered triangular waveform has a pulse width that is set inversely proportional to a diameter of target fibers to be stimulated in response to the delivery of electrical therapy.

31. The system of claim 22, wherein, if a peak current delivery of the electrical therapy involves less voltage than available from a power supply, the variable compliance regulator is configured to provide a substantially fixed compliance voltage to the supply rail to enable the compliance voltage to continuously vary the output waveform.

32. A stimulation apparatus comprising:
a variable compliance regulator connected to supply a compliance voltage to a voltage rail, the variable compliance regulator being configured to dynamically vary the compliance voltage over time to track a waveform shape and amplitude of a time-varying stimulus waveform;
a controller configured to generate the stimulus waveform comprising a substantially centered triangular shape, the controller controlling at least one of the stimulus waveform and the variable compliance regulator based on at least one sensed parameter; and
a pulse generator coupled to receive power from the power supply rail and configured to provide an output waveform to at least one output port in response to the stimulus waveform provided to a control input thereof, the output waveform having a waveform shape and amplitude corresponding to the waveform shape and the amplitude of the time-varying stimulus waveform and having energy that varies as a function of the compliance voltage.

33. The apparatus of claim 22, wherein the centered triangular waveform has a pulse width, the controller setting the pulse width to be inversely proportional to a diameter of target neuron fibers to be stimulated in response to the delivery of electrical therapy.

34. The apparatus of claim 23, wherein the target neuron fibers reside in the brain for deep brain stimulation, the controller being configured to set the pulse width with a maximum duration to minimize energy required for activation of the target neurons.

35. The apparatus of claim 23, wherein the target neuron fibers reside in the spinal cord, the controller being configured to set the pulse width with a maximum duration to minimize energy required for activation of the target neurons in the spinal cord.

* * * * *